(12) United States Patent
Foster

(10) Patent No.: US 8,442,657 B2
(45) Date of Patent: May 14, 2013

(54) STIMULATION AND SENSING LEAD WITH NON-COILED WIRE CONSTRUCTION

(75) Inventor: Arthur J. Foster, Centerville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 985 days.

(21) Appl. No.: 12/189,454

(22) Filed: Aug. 11, 2008

(65) Prior Publication Data

US 2009/0099635 A1   Apr. 16, 2009

Related U.S. Application Data

(60) Provisional application No. 60/980,351, filed on Oct. 16, 2007.

(51) Int. Cl.
*A61N 1/05* (2006.01)

(52) U.S. Cl.
USPC .......................................... 607/122

(58) Field of Classification Search ........... 607/115–138
See application file for complete search history.

(56) References Cited

U.S. PATENT DOCUMENTS

| | | |
|---|---|---|
| 3,890,977 A | 6/1975 | Wilson |
| 4,365,639 A | 12/1982 | Goldreyer |
| 4,386,615 A | 6/1983 | Sowton |
| 4,608,986 A | 9/1986 | Beranek et al. |
| 5,251,643 A | 10/1993 | Osypka |
| 5,303,704 A | 4/1994 | Molacek et al. |
| 5,330,523 A | 7/1994 | Campbell et al. |
| 5,545,201 A | 8/1996 | Helland et al. |
| 5,849,032 A * | 12/1998 | Van Venrooij ................ 607/123 |
| 6,564,107 B1 | 5/2003 | Bodner et al. |
| 6,671,562 B2 | 12/2003 | Osypka et al. |
| 6,701,191 B2 | 3/2004 | Schell |
| 6,717,056 B2 | 4/2004 | Rivelli et al. |
| 2002/0099430 A1 * | 7/2002 | Verness ......................... 607/122 |
| 2004/0068313 A1 | 4/2004 | Jenney et al. |
| 2005/0159801 A1 * | 7/2005 | Marshall et al. .............. 607/122 |
| 2007/0282411 A1 * | 12/2007 | Franz et al. ................... 607/116 |

FOREIGN PATENT DOCUMENTS

EP        0479435        4/1992

OTHER PUBLICATIONS

International Search Report and Written Opinion from international application No. PCT/US2008/072773, mailed Oct. 29, 2008, 16 pp.
Adler et al., "Thin Bipolar Leads: A Solution to Problems with Coaxial Bipolar Designs," PACE 15, Nov. Part II, 1992, pp. 1986-1990.

* cited by examiner

*Primary Examiner* — Rex R Holmes
(74) *Attorney, Agent, or Firm* — Faegre Baker Daniels LLP

(57) ABSTRACT

A cardiac rhythm management device that can comprise a lead and a pulse generator. The lead can comprise lead body, a composite conductor, a stylet guide, two or more electrodes and a proximal connector. The composite conductor can comprise two or more conductors which can electrically couple the electrodes to the proximal connector. The electrodes can be disposed on a distal portion of the lead body and can be longitudinally spaced from one another. The proximal connector can be configured to couple to the pulse generator.

10 Claims, 3 Drawing Sheets

STIMULATION AND SENSING LEAD WITH NON-COILED WIRE CONSTRUCTION

RELATED APPLICATIONS

This application claims the benefit under 35 U.S.C. §119 of Provisional Application No. 60/980,351, filed Oct. 16, 2007, entitled "Stimulation and Sensing Lead with Non-Coiled Wire Construction," the entirety of which is herein incorporated by reference.

TECHNICAL FIELD

The present invention relates to cardiac rhythm management devices for stimulating body tissues and/or sensing physiological attributes. More specifically, the invention relates to electrical conductors for use in such devices.

BACKGROUND

Various physiological functions can be managed and/or monitored using medical devices. Many such medical devices include conductor elements, where the conductor elements are configured to deliver an electrical signal to a target location within the body and/or sense an electrical signal at a target location within the body. For example, implantable medical devices have been used in association with cardiac rhythm management, which can include cardiac pacing, cardiac defibrillation, and/or cardiac therapy, among other procedures. Various designs for such conductor elements are known in the art. There exists a need for alternative designs for conductor elements that can be used in such medical devices.

SUMMARY

In one embodiment of the invention, a medical electrical lead comprises a proximal connector having a proximal end and configured to couple the lead to a CRM device, an insulative lead body extending distally from the proximal connector, and first and second longitudinally spaced electrodes coupled to the lead body. An uncoiled composite conductor wire is disposed within the lead body and includes a generally tubular first conductor electrically coupled to the first electrode, a second conductor disposed at least partially within the first conductor and electrically coupled to the second electrode, and an insulating layer between the first and second conductors. A stylet lumen extends distally from the proximal end within the lead body, the lumen sized to slidably receive a stylet or guide wire.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
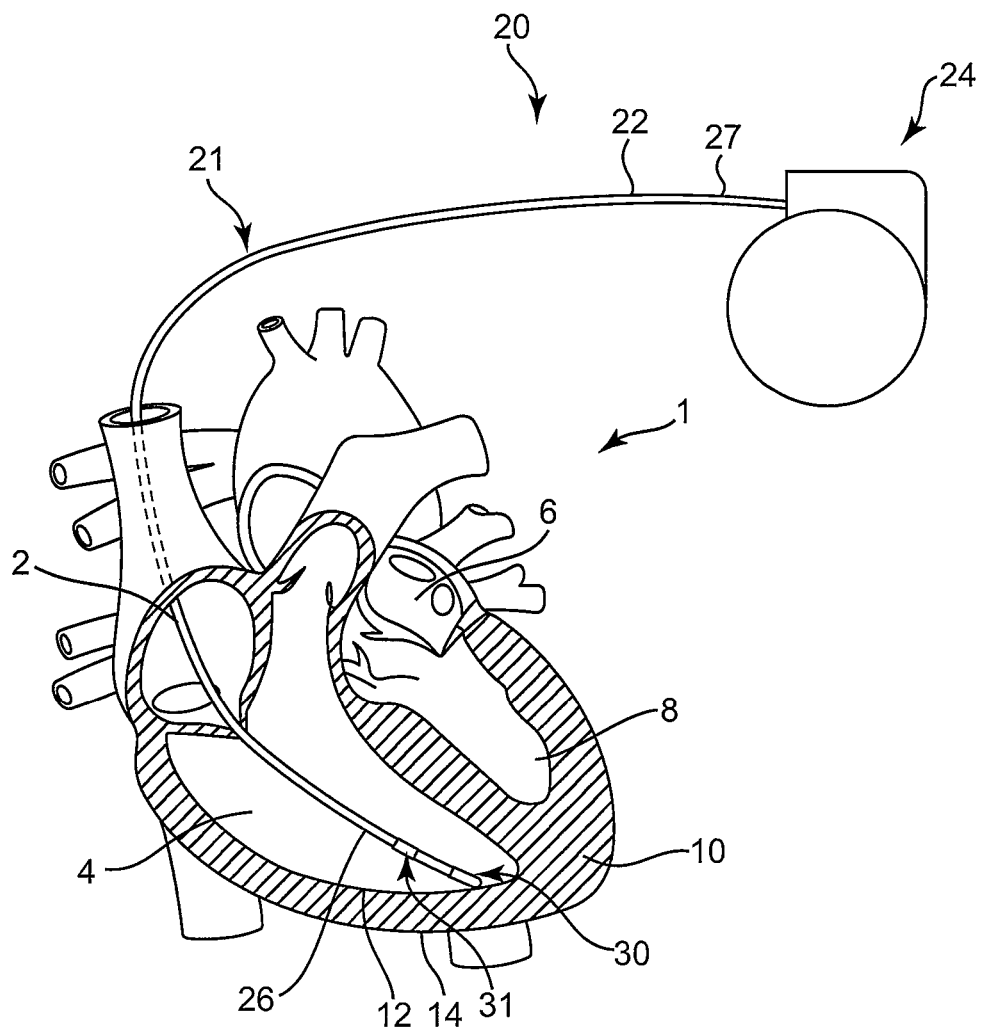
FIG. 1 shows an exemplary cardiac rhythm management device implanted in a heart according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a combined cutaway view of a human heart 1 and a perspective view of an exemplary cardiac rhythm management (CRM) device 20. The CRM device 20 includes a lead 21 and a pulse generator 24. The lead 21 has a lead body 22 with a distal end portion 26 and a proximal end portion 27. In various embodiments, the lead 21 can include one or more electrodes disposed on the lead body 22. In the example shown in FIG. 1, the lead 21 has a tip electrode 30 disposed on or near the distal end of the lead body 22 and a ring electrode 31 that is disposed on the lead body 22 proximal of the tip electrode 30. The CRM device 20 may sense electrical signals of the heart 1 and/or deliver electrical pulses to the heart 1 in an attempt to correct an arrhythmia and restore sinus rhythm.

In FIG. 1, the tip electrode 30 is coupled to the inner layer or endocardium 12 of the right ventricle 4 of the heart 1. In other embodiments, the lead 21 can be implanted or placed within any chamber of the heart 1. For example, the lead 21 can be implanted in the right atrium 2, the left atrium 6 or the left ventricle 8.

In addition, the lead 21 can be implanted in or be placed on the epicardium 14, for example the epicardium 14 of the right atrium 2, the right ventricle 4, the left atrium 6 or the left ventricle 8. In such cases, the lead 21 can be delivered through the circulatory system of the heart to the location of interest, or it can be implanted or placed on the epicardium 14 by gaining access to the pericardial space. In some embodiments, the lead 21 may be implanted through the epicardium 14 or endocardium 12 and into the myocardium 10.

CRM devices that comprise two or more electrodes can be multipolar. In some multipolar systems, two electrodes function as the two poles of the CRM device. This is often called a "bipolar" system. In other multipolar systems, an electrode of the CRM device acts as one pole of an electrical system, and the second pole of the electrical system can be located remotely from the electrode. For example, the second pole of the electrical system can be located on a pulse generator, or it can be located in another portion of the patient's body or on the surface of the patient's body. The CRM device can be programmed to sense which of the electrodes most efficiently stimulates tissues. The CRM device can then use the most efficient electrode as one pole of the device and the remote pole as the second pole of the device. Various configurations for multipolar devices are known in the art.

When the CRM device is energized, an electrical potential can be created between the two electrical poles of the device. This potential can create an electrical field and, in some cases, can create a current between the poles. When this electrical field or current is sufficiently strong, and when myocardial cells are disposed within the field or current, the myocardial cells can become depolarized, which leads to the contraction of the heart muscle. In addition, myocardial cells have the ability to propagate this electrical signal, causing depolarization of adjacent myocardial cells. This self propagation within the myocardium allows a target area of the heart to contract upon the stimulation of only a portion of the target area.

Alternatively, or in addition to stimulating the cardiac tissues, in some embodiments the electrodes of the CRM device can be configured to sense certain physiological attributes of the heart. For example, the heart's natural electrical signals can be received by an electrode and transmitted to a remote location (e.g., the pulse generator 24). In discussing embodiments of this invention, reference will be made primarily to electrodes stimulating body tissues. However, those of ordinary skill in the art will recognize that some or all of these electrode configurations could also be used to receive electrical signals from the heart.

In the illustrated embodiment, the lead body 22 extends through the vasculature of the body and into the heart 1. In some cases, the vasculature in which the lead body is disposed is tortuous and/or the vasculature has a small diameter. In addition, the lead body 22 can pass through or near portions of the body that are in motion, such as the heart 1. The movement of these portions of the body can cause the lead body 22 to experience a potentially large number of bending cycles.

To accommodate such conditions, the lead body 22 has an improved combination of size and physical properties such as flexibility and fatigue resistance, as discussed below. Further, the low profile of some of the embodiments of the invention can reduce or eliminate issues arising from magnetic resonance imaging. For example, some of the embodiments of the invention create little or no heating and/or imaging distortion or artifacts when subjected to MRI.

Figure 2:
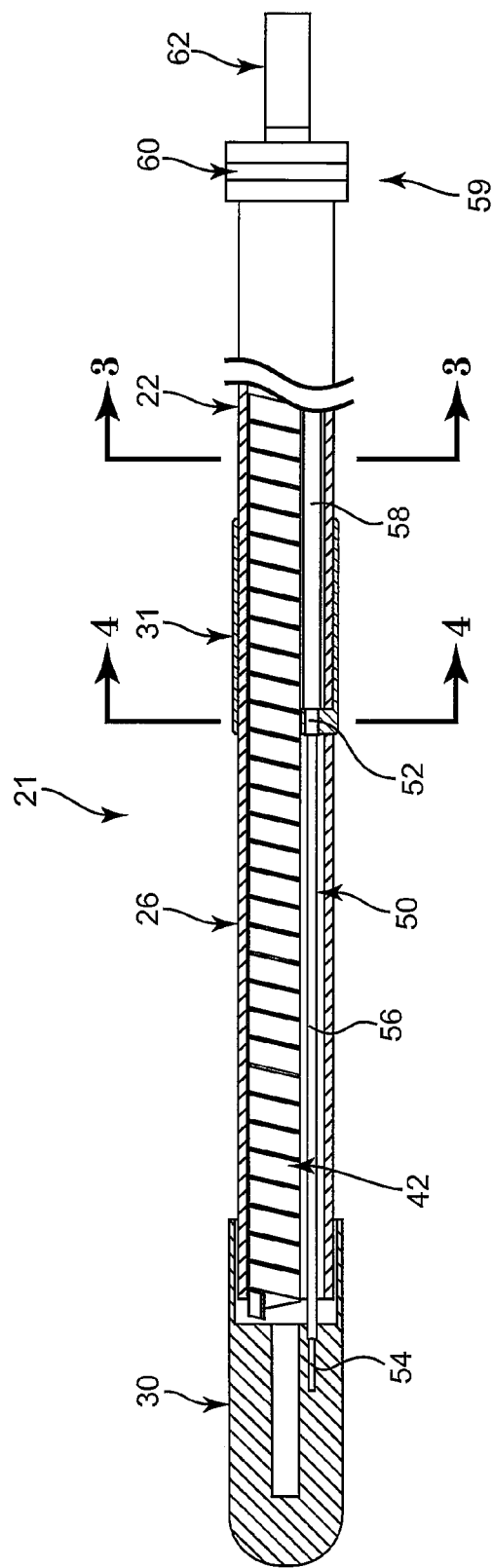
FIG. 2 shows a longitudinal cross-sectional view of a medical device lead.

FIG. 2 shows a longitudinal cross-section of the lead 21 according to embodiments of the invention. As shown in FIG. 2, the lead 21 comprises a lead body 22, a stylet guide 42, a composite conductor 50, a pair of electrodes 30, 31 and a proximal connector 59.

The lead body 22 is formed from a flexible, insulative, biocompatible material, for example PTFE, ePTFE, PEEK, silicone, polyurethane, or a blend of silicone and polyurethane, or any other suitable material. The stylet guide 42 and the composite conductor 50 extend through substantially the entire length of the lead body 22. As further discussed below, the stylet guide 42 provides a stylet lumen 43 sized and configured to receive a stylet or a guidewire to facilitate transvenous delivery of the lead 21. Also as discussed further below, the composite conductor 50 electrically couples the electrodes 30, 31 to the proximal connector 59. Further, the proximal connector 59 is shaped and configured to mechanically and electrically couple to a pulse generator (e.g., pulse generator 24 shown in FIG. 1).

Figure 3:
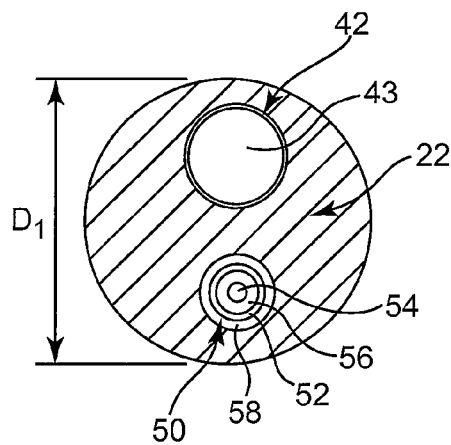
FIG. 3 shows a cross-sectional view of a portion of the medical device lead of FIG. 2.
Figure 4:
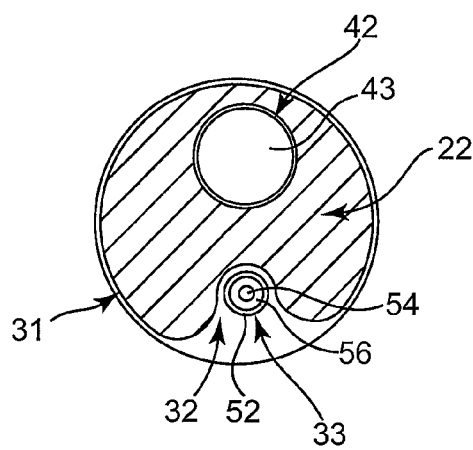
FIG. 4 shows a cross-sectional view of another portion of the medical device lead of FIG. 2.

The stylet guide 42 can have any configuration providing the desired functionality and flexibility. As shown in FIG. 2, the stylet guide 42 is a metallic wire that is wound into a coil in order to define a stylet lumen 43 (the stylet lumen 43 is best shown in FIGS. 3 and 4). The wire can be of a variety of cross-sectional shapes, including round, oval, or, as shown in FIG. 2, rectangular. In other embodiments, the stylet guide 42 can comprise a substantially continuous tubular member. Portions of the tubular member can be removed to make the tubular member more flexible. For example, portions of the tubular member can be removed to form a coil shaped member or intermittent cuts can be made in the tubular member to make the tubular member flexible.

As mentioned above, the stylet guide 42 extends through substantially the entire length of the lead body 22. In other embodiments, the stylet guide 42 can extend through only a portion of the lead body 22, for example a distal portion of the lead body 22, and a proximal portion of the stylet lumen 43 can be a channel that is formed through the lead body 22. In other embodiments, the stylet guide 42 can be absent entirely, and the stylet lumen 43 can be a channel that is formed through the lead body 22.

The stylet lumen 43 has an opening in the proximal portion (not shown) of the lead body 22 in order to allow the placement of a stylet or guidewire in the stylet lumen 43. As is known in the art, a stylet or guidewire can be used to facilitate placement of the lead 21 at a target location. As shown in the example of FIG. 2, the stylet lumen 43 has a closed distal end, allowing a stylet or guidewire to impart a pushing force on the distal end of the lead 21 during placement of the lead 21. In other embodiments, the stylet lumen 43 can have an open distal end (not shown). This open distal end (i.e., an opening through the distal tip of the lead body 22) can facilitate over the wire delivery of the lead 21.

As shown in FIG. 2, the composite conductor 50 extends through substantially the entire length of the lead body 22 and, as further discussed below, the composite conductor 50 can electrically couple the electrodes 30, 31 to the proximal conductor 59. The composite conductor 50 has a straight configuration within the lead body 22. The composite conductor 50 can be substantially or entirely straight, or uncoiled, along its entire length or along a distal portion of the composite conductor 50. Those of skill in the art will recognize that a conductor 50 with an uncoiled configuration, as shown in FIGS. 2-4, can yield a low profile compared to a conventional coiled conductor.

The composite conductor 50 comprises a first tubular-shaped conductor 52 and a second conductor 54 that is disposed within the first conductor 52. Further, the composite conductor 50 has an inner insulating layer 56 that is disposed between the first and second conductors 52, 54. The inner insulating layer 56 ensures that the first and second conductors 52, 54 are electrically isolated from one another. The composite conductor 50 can also optionally have an outer insulating layer 58 which can provide additional insulation to ensure that the composite conductor 50 is electrically isolated from other elements in the lead body 22 and/or from the surrounding environment.

FIG. 3 shows a cross-section of the lead 21 taken along the line 3-3 in FIG. 2. As shown, the stylet guide 42 and the composite conductor 50 are disposed in the insulative lead body 22 eccentrically with respect to one another. Referring to the cross-section of the composite conductor 50, the second conductor 54 is a core member of the composite conductor 50. As mentioned above, an insulating layer 56 is disposed between the first and second conductors 52, 54, and an outer insulating layer 58 forms an insulating layer around the first conductor 52. As shown, the first and second conductors 52, 54 and the insulating layers 56, 58 are arranged coaxially with respect to one another, although other arrangements are possible.

As noted above, in some cases it is desired to maintain the lowest possible profile of the lead body 22. The noncoiled nature of composite conductor 50 can allow for a small diameter $D_1$ relative to standard lead body designs. For example, $D_1$ can be 0.030 inches or less, or between 0.025 and 0.030 inches, or any other suitable dimensions. The noncoiled configuration of the composite conductor 50 can also define a shorter electrical pathway compared to a coiled conductor.

Turning again to FIG. 2, the second conductor 54 extends distally of the inner insulating layer 56, the first conductor 52 and the outer insulating layer 58. As such, a distal portion of the second conductor 54 provides a second conductor exposed surface. The second conductor exposed surface is mechanically and electrically coupled to the tip electrode 30, as described in more detail below. Further, the first conductor 52 extends distally of the outer insulating layer 58 with a distal portion of the first conductor 52 providing a first conductor exposed surface. The first conductor exposed surface is mechanically and electrically coupled to the ring electrode 31, as described in more detail below. In addition, the inner insulating layer 56 extends distally of the first conductor 52 a sufficient distance to electrically insulate the exposed surfaces of the first and second conductors 52, 54. As such, the inner insulating layer 56 terminates between the first electrode distal end and the second electrode distal end, or the electrode exposed surfaces are longitudinally spaced apart from one another.

The first and second conductors 52, 54 can comprise any materials with suitable electrical or mechanical properties. In some embodiments, metal alloys such as a linear elastic or superelastic Nitinol can be used. Other superelastic or flexible and fatigue resistant materials can also be used, such as other superelastic or flexible and fatigue resistant metal alloys. Some of these materials have a lower electrical conductivity (higher electrical resistance) compared to the electrical conductivity of conventional lead conductor materials (e.g., MP35N, platinum, a platinum core clad with MP35N, silver, a silver core clad with MP35N, or other conventional materials). However, as discussed above, the noncoiled configuration of the composite conductor 50 can result in a shorter electrical pathway compared to coiled conductors. As would be appreciated by those of skill in the art, the shorter pathway can provide less resistance to the flow of electricity, which can partially or entirely compensate for the higher resistance of some of the materials mentioned above. In addition, in some embodiments, the low profile composite conductor can be compatible with MRI.

Further, the insulating layers 56, 58 can comprise any insulating material suitable for use in medical electrical leads, for example an insulative polymer. Examples of suitable polymers are polyimide, PEEK, PTFE, ePTFE, silicone, polyurethane, of blends thereof, or any other suitable material. In some cases, the composite conductor 50 can be formed such that the inner insulating layer 56 is partially or entirely isolated from the environment For example, as further discussed below, the composite conductor 50 can be manufactured such that the inner insulating layer 56 fuses to the first and second conductors 52, 54. In such a case, the inner insulating later 56 is partially or entirely isolated from the surrounding environment by the first and second conductors 52, 54.

In some embodiments, the first and second conductors 52, 54 comprise Nitinol and the inner and outer insulating layers comprise polyimide.

In some embodiments, the composite conductor 50 can be manufactured using a drawing process. Before drawing, a composite billet can be assembled. The composite billet can comprise a first tubular member that corresponds to the first conductor 52 and an elongate member (e.g., a rod) that corresponds to the second conductor 54. The elongate member can be placed inside the tubular member to form the composite billet. Further, the material corresponding to the inner insulating layer 56 can be provided by coating the outer surface of the elongate member or by coating the inner surface of the tubular member. Alternatively, the material for the insulating layer 56 can be provided by disposing a second tubular member corresponding to the insulating layer 56 between the first tubular member and the elongate member.

The composite billet can be drawn down to the desired dimensions. In the process of drawing down the composite billet, the first tubular member, the elongate member and the material corresponding to the inner insulating layer 56 tend to fuse together to form the integral composite conductor. Using this process, the composite billet can be drawn down to form a composite conductor with a diameter of less than 0.015 inches, between 0.005 inches to 0.008 inches, between 0.005 inches and 0.012 inches, or other suitable dimensions.

In the example shown in FIG. 2, the electrodes 30, 31 are disposed on a distal portion of the lead body 22. The tip electrode 30 shown in FIG. 2 has a cylindrical shape with a rounded distal end. Further, the tip electrode 30 could also have a fixation member (not shown) disposed on the distal end of the tip electrode 30 that can allow the tip electrode 30 to be securely implanted in body tissue. As examples, a helical or barbed fixation member can be provided. Other fixation members are known in the art.

The exposed distal surface of the second conductor 54 can be electrically coupled to the tip electrode 30, for example by welding, brazing, or crimping, or by any other method know in the art. Further, the exposed distal surface of the second conductor 54 can be electrically coupled to the tip electrode 54 using a structure such as an eyelet coupler, as further described below with respect to FIG. 4.

The ring electrode 31 shown in FIG. 2 has a tubular shape and is disposed along the lead body 22 at a position proximal the tip electrode 30. FIG. 4 is a cross-sectional view of the lead 21 taken along the line 4-4 in FIG. 2. In FIG. 4, the insulative lead body 22 and the stylet guide 42 extend through the tubular shaped ring electrode 31. In the illustrated embodiment, the ring electrode 31 also has an eyelet coupler 32 that forms an opening 33, for example an eyelet or other lumen, through which the composite conductor 50 extends. As mentioned above, the composite conductor 50 has a first tubular conductor 52 that extends distally of the outer insulating layer 58, forming an exposed first conductor surface. This exposed first conductor surface is disposed in the opening 33, and the exposed first conductor surface is electrically coupled to the ring electrode 31 through this eyelet coupler 32.

As shown in FIG. 2, the eyelet coupler 32 is shorter than the length of the ring electrode 32, and it is disposed on a distal portion of the inside surface of the ring electrode 31. In other embodiments, the eyelet coupler 32 can be disposed on a proximal or medial portion of the inside surface of the ring electrode 31, or the eyelet coupler 32 can extend along the entire length of the inside of the ring electrode 31. The first conductor exposed surface can be mechanically and electrically coupled to the eyelet coupler 32 by welding, brazing, or crimping, or by using any other appropriate attachment technique known in the art. As will be appreciated by those of skill in the art, other configurations can be employed to electrically couple the conductor 52 to the ring electrode 32.

The composite conductor electrically couples the first and second electrodes 30, 31 to the proximal connector 59. The proximal connector 59 provides individual electrical contacts 60, 62 for the first and second conductors 52, 54 to facilitate electrical connection of the lead body 22 to a source of electrical energy, for example a pulse generator 24. As would be appreciated by those of skill in the art, the first contact 60 can be electrically coupled to the first conductor 52 and the second contact 62 can be electrically coupled to the second conductor 54 by any manner known in the art.

In some embodiments, the stylet guide 42 can comprise an electrically conductive material, and the stylet guide 42 can electrically couple a third electrode (not shown) to the proximal connector 59. For example, the third electrode could be a ring electrode disposed along the lead body 22 at a position distal or proximal of the ring electrode 31. Also, the proximal connector 59 can have a third contact, for example a second ring-type contact that is similar to the contact 60 or a separate contact on the pin 62. This third contact can be electrically coupled to a proximal portion of the stylet guide 42. In other embodiments, the stylet guide 42 can be a co-radial multi-conductor coil, and can be electrically coupled to additional electrodes, thus forming an additional multipolar lead configuration.

Figure 5:
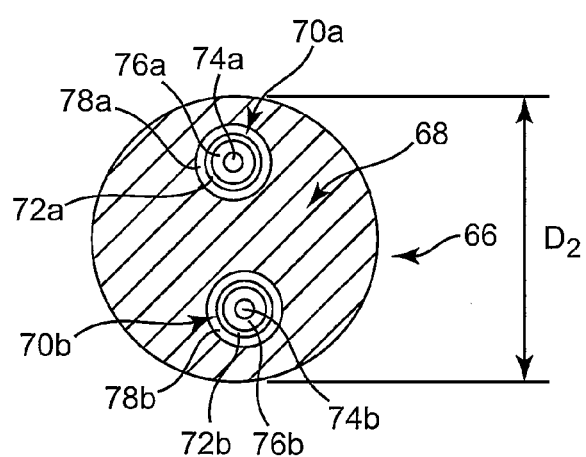
FIG. 5 shows a cross-sectional view of a medical device lead according to embodiments of the invention.

FIG. 5 shows a cross-section of another lead design in accordance with embodiments of the invention. The lead 66 has a lead body 68, which can be similar to the lead body 22 in design and materials of construction. The lead body 68 has two or more composite conductors 70a, 70b. The composite conductors 70a, 70b can be similar to the composite conductor 50 described above with respect to FIGS. 2-4. The composite conductors 70a, 70b each have a first tubular conductor 72a, 72b, a second conductor 74a, 74b disposed within respective tubular conductors 72a, 72b, and insulating layers 76a, 76b disposed between the first conductors 72a, 72b and second conductors 74a, 74b. The composite conductors 70a, 70b also have an optional outer insulating layer 78a, 78b. As mentioned above with respect to the composite conductor 50, the first tubular conductors 72a, 72b extend distally of the optional outer insulating layers 78a, 78b, forming exposed distal surfaces of the first tubular conductors 72a, 72b. These exposed surfaces can be electrically coupled to electrodes that can be disposed along the lead body 68.

The inner insulating layers 76a, 76b extend distally of the first tubular conductors 72a, 72b and the second conductors 74a, 74b extend distally of the inner insulating layers 76a, 76b, forming second conductor exposed surfaces. These second conductor exposed surfaces can be electrically coupled to electrodes that can be disposed along the lead body 68. In this manner, four electrodes can be electrically coupled to a proximal connector. In addition, in some embodiments of the invention, the lead can comprise more than two composite conductors.

In one example, the lead body 68 has a tip electrode and three or more ring electrodes disposed along the lead body 68. In other embodiments, the lead body 68 can have four or more ring electrodes disposed along the lead body 68. The tip and/or ring electrodes, and the manner in which the electrodes are connected to the exposed surfaces of the conductors, can be similar to those described above with respect to FIGS. 2-4.

The inclusion of multiple composite conductors 70a, 70b can allow for multiple electrically active sites along the lead body 68. At the same time, the relatively low profile of the composite conductors 70a, 70b can allow the overall lead body profile, $D_2$, to be small relative to standard lead designs. For example, the diameter $D_2$ can be any of the dimensions mentioned above with respect to dimension $D_1$ in FIG. 3.

Further, the lead body 68 of FIG. 5 is shown without a stylet lumen. Delivery of such a lead 66 can be accomplished using techniques known in the art, including the use of a delivery catheter. In other embodiments, the lead body can comprise two or more composite conductors and a stylet lumen, for example a stylet lumen similar to the stylet lumen 43 described above.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations which fall within the scope of the claims, together with all equivalents thereof.

I claim:

1. A medical electrical lead comprising:
   a proximal connector having a proximal end and configured to couple the medical electrical lead to a CRM device;
   an insulative lead body extending distally from the proximal connector;
   first and second longitudinally spaced electrodes coupled to the lead body; and
   an uncoiled composite conductor wire disposed within the lead body and including a generally tubular, uncoiled first conductor electrically coupled to the first electrode, a second conductor disposed at least partially within the first conductor and electrically coupled to the second electrode, and an insulating layer between and fused to the first and second conductors such that the first and second conductors are operable to isolate the insulating layer from a surrounding environment.

2. The medical electrical lead of claim 1, wherein the second conductor is a solid inner core of the composite conductor wire.

3. The medical electrical lead of claim 1, wherein the insulating layer comprises polyimide.

4. The medical electrical lead of claim 1, wherein the first electrode is a ring electrode that is disposed proximal of the second electrode.

5. The medical electrical lead of claim 4, wherein a distal portion of the first conductor is electrically coupled with a connector member of the first electrode, wherein the insulating layer and the second conductor extend distal of a first conductor distal end, and wherein the second conductor extends distal of an insulating layer distal end and is electrically coupled to the second electrode.

6. The medical electrical lead of claim 5, wherein the connector member is an eyelet coupler.

7. The medical electrical lead of claim 1, wherein the second electrode is a tip electrode that is disposed distal of the first electrode.

8. The medical electrical lead of claim 1, further comprising a second composite conductor electrically connected to third and fourth electrodes.

9. A medical electrical lead comprising:
   a proximal connector having a proximal end and configured to couple the medical electrical lead to a CRM device;
   an insulative lead body extending distally from the proximal connector;
   first and second longitudinally spaced electrodes coupled to the lead body; and
   an uncoiled composite conductor wire disposed within the lead body and including a generally tubular, uncoiled first conductor electrically coupled to the first electrode, a second conductor disposed at least partially within the first conductor and electrically coupled to the second electrode, and an electrically insulating layer disposed between and fused to the first and second conductors such that the first and second conductors are operable to isolate the insulating layer from a surrounding environment, the first and second conductors each comprising a superelastic metal alloy.

10. The medical electrical lead of claim 9, wherein both of the first and second conductors comprise Nitinol.

* * * * *